United States Patent [19]

Vaillancourt

[11] Patent Number: 5,575,769
[45] Date of Patent: Nov. 19, 1996

[54] CANNULA FOR A SLIT SEPTUM AND A LOCK ARRANGEMENT THEREFORE

[76] Inventor: Vincent L. Vaillancourt, 14 Bunyan Dr., Livingston, N.J. 07039

[21] Appl. No.: 453,624

[22] Filed: May 30, 1995

[51] Int. Cl.⁶ .................................................. A61M 37/00
[52] U.S. Cl. .................................................. 604/86; 604/905
[58] Field of Search .......................... 604/86, 88, 283, 604/905, 274

[56] References Cited

U.S. PATENT DOCUMENTS

| | | | |
|---|---|---|---|
| 4,645,494 | 2/1987 | Lee et al. | 604/86 X |
| 5,135,489 | 8/1992 | Jepson et al. | 604/905 X |
| 5,178,607 | 1/1993 | Lynn et al. | 604/86 |

Primary Examiner—John D. Yasko
Attorney, Agent, or Firm—McAulay Fisher Nissen Goldberg & Kiel, LLP

[57] ABSTRACT

A smooth tipped hollow needle is provided for piercing a slit septum of a medical connector or the like. The smooth tipped needle may be of closed end type or of open end type. Due to the smooth septum-penetrating surfaces, the needle minimizes the risk of debris being scrapped or abraded from the internal wall of the septum during penetration. An internal locking mechanism is also provided for locking a needle within a connector after passage through a septum. The locking mechanism employs a washer with protuberances to mate within dimples on the needle.

18 Claims, 2 Drawing Sheets

CANNULA FOR A SLIT SEPTUM AND A LOCK ARRANGEMENT THEREFORE

This invention relates to a cannula for use with a slit septum. More particularly, this invention relates to a smooth tipped cannula for use with a slit septum. Still more particularly, this invention relates to a lock arrangement for locking a cannula relative to a penetrated septum.

As is known, various types of cannulae, i.e. hollow needles, have been known for medical use, for example, for intravascular use, urological use and the like. In many cases, the hollow needle is mounted on a syringe or is connected with a tube supplied with liquid, such as a medicament, saline solution, or other type of fluid which can be injected into a patient. Typically, the hollow needle is used to puncture or pierce a septum, for example made of an elastomeric material, in order to gain access to a tube or connector connected to a patient. In other cases, a hollow needle is mounted in a recessed manner in a connector communicating with a patient while a septum seals off the chamber in which the needle is located. In such cases, a male luer connector or other type of tubular connector has been used to engage and push the septum back over the needle thereby exposing the needle, for example for communication with the interior of the male luer connector. Other connection units are also known where either the needle moves relative to a septum or the septum moves relative to a needle to make a connection.

Studies have shown that when a hollow needle pierces through an elastomeric septum, a "coring" effect takes place. That is to say, the needle tends to core the septum. A problem which arises in this regard is that the cored out material is then in the path of fluid to or from a patient. Accordingly, in order to avoid such a coring effect, the septums have been provided with a slit which typically penetrates the entire length of the septum and facilitates passage of the needle through the septum.

However, additional studies have shown that a hollow needle having a sharp tip will silver or scrape material from the internal side wall of the septum when passing into and through the slit. The resulting debris is thus in the path of the fluid through the hollow needle. It has also been found that a blunt ended needle although having a rounded outer surface, typically has a sharp edge at the inner surface, i.e. on the inside diameter of the end of the needle. Hence, blunt needles, particularly plastic units as well as metal units, may well scratch the skin of a user and cause micro cuts thereby defeating the purposes of using this type of needle. In addition, during passage through a slit septum, debris will be scrapped off the side walls of the septum defining the slit.

It has been found that as the number of penetrations of a needle through a septum increases, the elastomeric surface of the septum tends to either become gouged out, particularly with low durometer rubber septums (Shore A 25–35) or the surface is abraded and sometimes streaked when the same path is taken by each consecutive needle engagement. This latter effect occurs mostly with higher durometer septums (Shore A 35–50/60).

In many cases, after a needle has penetrated through a septum in order to make a fluid connection between a fluid delivery device and a patient, the needle is left in place for a period of time. Where the patient is active, there is a risk that the needle may be inadvertently withdrawn from the septum thereby breaking the connection. Generally, the firmness of the connection relies upon the frictional force between the needle and the septum. If the engagement is loose, the needle may be readily disengaged. Where the septum is under a circumferential compression force, such as described in pending U.S. Pat. No. 08/245,893, filed May 19, 1994, the engagement force is increased. However, a very active patient or a patient with intent may be able to withdraw the needle from the septum. In the past, it has been known to provide a locking arrangement to maintain a needle of one connector in a septum of another connector. Usually, such locking arrangements have been of an external type whereby the two connectors are locked together after penetration of the needle through the septum. However, such external locking arrangements require additional manufacturing steps while also enlarging the overall size of the connection.

Accordingly, it is an object of the invention to avoid the production of debris during passage of a needle through a slit septum.

It is another object of the invention to increase the useful life of a connector employing a slit septum.

It is another object of the invention to permit a multiplicity of penetrations of a needle relative to a slit septum without the creation of detrimental debris from the septum.

It is another object of the invention to provide a relatively simply locking means for locking a needle relative to a septum after passage of the needle through the septum.

It is another object of the invention to provide a connection wherein a needle is locked relative to a septum by an internal locking mechanism.

Briefly, the invention is directed to a combination of elements which includes a septum of elastomeric material having a slit and a hollow needle for penetrating the septum through the slit. In accordance with the invention, the needle is provided with smooth surfaces for penetrating the septum. In this regard, the needle may be of a closed-end type or an open-end type.

In one embodiment, wherein the needle is of a closed-end type, the closed distal end of the needle is provided with a smooth surface for penetrating the septum without removing debris from the septum. In addition, the needle has at least one opening in a side wall for the passage of fluid into or from within the needle.

The distal end of the needle may have, for example, a hemispherical shape or any other suitable curvilinear shape. Alternatively, the distal end of the needle may have a flattened transverse surface at the end and a rounded periphery extending from the flattened transverse surface through a side wall of the needle.

In another embodiment where the needle is of open-end type, the needle may have an open distal end for passage of fluid directly therethrough with a peripheral wall terminating in a smooth rounded surface for penetrating into the septum without removing debris therefrom. In this embodiment, the peripheral wall typically has a uniform thickness and may be of cylindrical shape, tapered shape or the like. In addition, the peripheral wall may be made by being folded inwardly of itself in order to define a smooth rounded surface.

Obviously, the relative sizes between the needle and the septum are to be taken into account when fabricating the septum. However, for the usual range of sizes of needle and septums, the needles which are employed in accordance with the invention generally have an outside diameter in a range of from 0.032" to 0.058" inches while the slit septums are of a cylindrical shape with an outside diameter in the range of from ¼ to ½ inches, a Shore A hardness of from 25 to 60, and a length (i.e. thickness) of from 0.075" to 0.160" inches.

In accordance with another embodiment of the invention, in order to secure a needle in place after penetration through a septum, a means is provided for releasably locking the needle relative to the septum, for example, to preclude accidental withdrawal of the needle.

In one embodiment, the locking means is employed in a combination which includes a tubular member for conducting fluid therethrough, an elastomeric septum secured to one end of the tubular member to seal the end against the passage of fluid and a hollow needle for penetrating the septum in order to communicate with the interior of the tubular member. In this case, the locking means is provided within the tubular member for releasably engaging the needle after penetration of the needle through the septum in order to prevent accidental withdrawal of the needle from the tubular member.

In this embodiment, the locking means may be in the form of a washer within the tubular member having at least one protuberance for engaging a dimple provided for such in a side wall of the needle. This washer may be spaced coaxially from the septum or may be provided adjacent to or made a part of the septum. When in use, after a needle has penetrated through the septum and is positioned in place, the needle is rotated so as to engage the protuberance or protuberances of the washer in the respective dimples in the needle thereby achieving a releasable locking effect. The relative dimensions of the dimples and protuberances are such that a firm gripping engagement is provided so that the needle cannot be easily removed from the septum without exerting some positive force.

Typically, in order to remove the needle when required, the needle would be rotated so as to disengage the protuberances of the washer from the dimples of the needle. Thereafter, the needle would be withdrawn through the septum. Of course, should a patient desire to exert a sufficient force to withdraw the needle, such could not be prevented in any event. However, the risk of an accidental or inadvertent removal of the needle such as during the time a patient is asleep should be minimized.

It is to be noted that the locking means may be in employed with a hollow needle which does not necessarily have rounded portions of the above embodiments. In fact, the locking means may be employed with any conventional needle, such as those having a sharp tip or the conventional blunt tip. Likewise, the locking means may be employed with septums which have not been pre-slit.

In those embodiments where the septums are provided with a slit and the hollow needle has smooth surfaces for penetrating the slit, the locking means may be external of the tubular member. In this regard, any suitable conventional external locking member may be used such as bayonet type members, snap fit members and the like. In this regard, reference is made to U.S. Pat. No. 5,122,123 for a suitable type of external locking means.

The connections which are made in accordance with the invention may employ the septum and needle in various matters relative to each other. For example, the septum may be mounted on the end of a tubular member which contains a chamber while the hollow needle is mounted on another member for penetrating into the septum in order to gain access to the chamber. In other arrangements, a tubular connector may be provided with a needle within a chamber while the septum is mounted on a collapsible sleeve in the manner of a boot so that the septum can be moved by a male luer connector, adaptor or the like into the tubular member so as to slide over and expose the needle to the penetrating member.

These and other objects and advantages of the invention will become more apparent from the following detailed description taken in conjunction with the accompanying drawings wherein.

Figure 1:
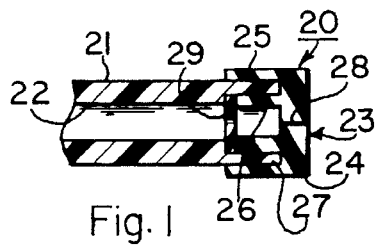
FIG. 1 illustrates a cross-sectional view of a tubular member having a slit septum mounted therein as well as an internal locking means in accordance with the invention.

Referring to FIG. 1, the connector 20 employs a tubular member 21, for example of plastic, which has a bore or chamber 22 for conducting fluid therethrough. Typically, such a tubular member 21 may be at the end of a flexible tube which forms part of a connection assembly which is implanted in a patient (not shown). Such tubes may be provided as part of an access device so as to provide an injection site for injecting medicaments, saline solutions or the like into the patient as well as a site at which blood or other fluids may be withdrawn or expelled from the patient.

The connector 20 also has an elastomeric septum 23 secured to the end of the tubular member 21 in order to seal the end against the passage of fluid. As indicated, the septum 23 has a disc-shaped wall 24 transverse to the tubular member 21, an external annular lip 25 for sealing over the end of the tubular member 21 and an internal annular wall 26 for sealing against the inside diameter of the tubular member 21. As indicated, the tubular member 21 may be provided with an internal annular recess 27 to receive the inner wall 26 of the septum 23.

Septums of this type are of generally conventional structure and need not be further described. Further, the wall 24 of the septum 23 is provided with a slit 28 which, in this embodiment, completely penetrates the wall 24 of the septum 23.

Figure 4:
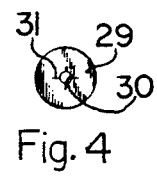
FIG. 4 illustrates a front view of a washer employed as a locking means in FIG. 3.

A locking means 29 is also provided internally of the tubular member 21. As indicated, the locking means 29 is in the form of a washer (see FIG. 4) of elastomeric material or any other suitable material for medical purposes. The washer 29 has a central bore 30 coaxially aligned with and spaced from the slit 28 within the wall 24 of the septum 23. As indicated, the washer 29 is received within the recess 27 of the tubular member 21 and is seated therein in a firm manner by the inner annular wall 26 of the septum 23. In addition, as indicated in FIG. 4, the washer 29 has one or more protuberances, for example, two protuberances 31 for purposes as explained below.

Figure 2:
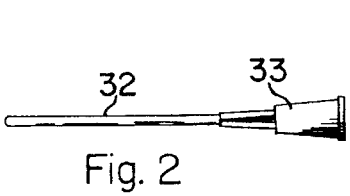
FIG. 2 illustrates a side view of a smooth tipped hollow needle for penetrating into and through the septum of FIG. 1 in accordance with the invention.

Referring to FIG. 2, the hollow needle 32, i.e. cannula, is mounted on a hub 33 or other suitable type of structure for penetrating into the septum 23 of the connector 20 of FIG. 1 via the slit 28. The hub 33 may be mounted on any suitable member, such as a syringe or the like, for either removing fluids from within the tubular member 21 of the connector 20 or injecting fluid into the tubular member 21. The closed end of the needle 32 is provided with smooth surfaces for penetrating through the wall 24 of the septum 23. Such a needle is described in U.S. Pat. No. 5,509,912. In this respect, the smooth surfaces are of a nature that multiple penetrations may be made without removing debris from the septum. For example, the smooth surfaces of the cannula are such that after twenty piercings, no debris is found of a size greater than 0.005 inches.

Figure 9:
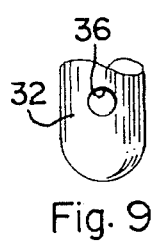
FIG. 9 illustrates a distal end view of a needle having a hemispherical distal end in accordance with the invention.
Figure 10:
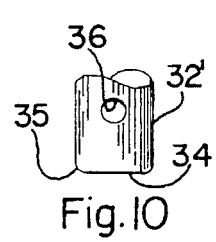
FIG. 10 illustrates a side view of a closed end type needle having a flat end in accordance with the invention.

The tip of the needle 32 may be made, for example, of the closed-end type, for example as shown in FIGS. 9 and 10. For example, as shown in FIG. 9, the end of the needle 32 may have a hemispherical shape. As shown in FIG. 10, the end of the needle 32' may have a flattened transverse surface 34 with a rounded periphery 35 extending from the flat surface 34 to a side wall of the needle 32'. In addition, one or more openings 36 are provided in the side wall of the needle 32, 32' for the passage of fluid into and from the needle.

Figure 11:
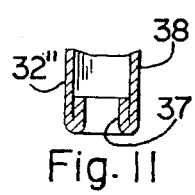
FIG. 11 illustrates a cross sectional view of an end of an open end type needle in accordance with the invention.
Figure 12:
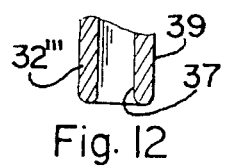
FIG. 12 illustrates a part cross-sectional view of the end of a further modified opened-end type needle in accordance with the invention.

Alternatively, the hollow needle 32 may be of an open-end type having a tip with a central opening 39 such as shown in each of FIGS. 11 and 12. As indicated in FIG. 11, the peripheral wall 38 of the needle 32" is folded inwardly of itself in order to define a rounded surface at the terminal end. As shown in FIG. 12, the peripheral wall 39 of the needle 32''' has a smooth rounded surface at the terminal end. In this embodiment, the peripheral wall has a uniform thickness.

The peripheral wall of the needle 32 may be cylindrical, tapered or any other shape which is conventional.

Figure 3:
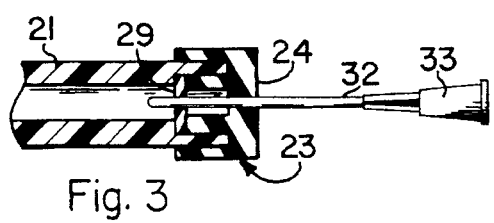
FIG. 3 illustrates a part cross-section view of the needle of FIG. 2 penetrated into the septum of FIG. 1 in accordance with the invention.

Referring to FIG. 3, in use, the hollow needle 32 is pierced through the transverse wall 24 of the septum 23 via the slit 28 so that the needle 32 passes into and through the bore of the washer 29. The penetration of the needle is to such an extent that the opening or openings 36, 37 within the needle 32 are exposed to the chamber 22 within the tubular member 21.

The hollow needle 32 is also provided with one or more dimples (not shown) at the distal end in order to cooperate with the protuberances (see FIG. 4) on the locking washer 29.

After penetration of the needle 32 through the septum 23 and washer 29, the needle 32 is rotated until the protuberances on the washer 29 mate within the dimples of the needle 32. A releasable locking engagement of the needle 32 within the septum 23 thereby takes place.

In order to unlock the needle 32 from the connector 20, the needle 32 is rotated so as to move the dimples from engagement with the protuberances of the locking washer. Thereafter, the needle 32 is withdrawn from the septum 23.

It is to be noted that the locking washer 29 may be used with a needle having dimples where the needle need not have a distal end which is open or closed in the manner as indicated in FIG. 9 and 12. Instead, the needle may be of any conventional structure. Likewise, the septum need not be slit, for example, in cases where a sharp ended needle is used to penetrate the septum.

Figure 5:
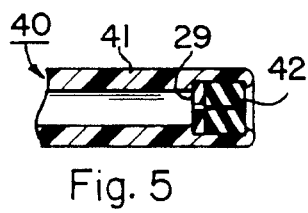
FIG. 5 illustrates a part cross-sectional view of a modified connector having a locking means and septum in accordance with the invention.

Referring to FIG. 5, a connector 40 may be constructed with a plastic tubular member 41 having a slit septum 42 which is recessed entirely within the tubular member 41. In this case, the septum 42 is of cylindrical shape and is received within a recess 43 of the tubular member 41 by a swaging over of a terminal end of the tubular member. Of course, any other suitable means may be used to secure the septum 42 within the tubular member 41. In addition, as shown, a locking washer 29 is abutted against the backside of the septum 42. Alternatively, the locking washer may be made as an integral part of the septum 42. That is, the septum may be molded in one piece to have a slit penetrating partway through while having a backside portion having an enlarged internal bore with protuberances formed therein to define a "washer like" portion.

Figure 6:
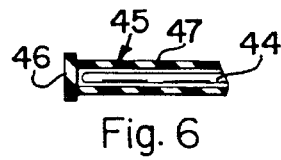
FIG. 6 illustrates a modified connector employing a needle within a collapsible boot for use with the connector of FIG. 4.

Referring to FIG. 6, a hollow needle 44 may be mounted in an assembly or connector (not shown) in which the hollow needle 44 is protected in a sealed manner by a collapsible boot 45. As indicated, the boot 45 includes a septum 46 in the form of a transverse wall mounted on a resilient collapsible sleeve 47. Thus, in order to gain access to the needle, the boot 45 must be collapsed so that the needle 44 pieces through the septum 46.

Figure 7:
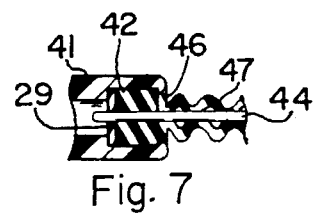
FIG. 7 illustrates a cross sectional view of the needle of FIG. 6 penetrating the septum and washer of FIG. 5 in accordance with the invention.

Referring to FIG. 7, when in use, the needle assembly (not shown) is brought against the connector 40 so that the septum 46 of the boot 45 engages in face-to-face relation within the slit septum 42 of the connector 40. The needle assembly is then pushed so that the needle 44 pierces not only through the septum 46 of the needle assembly but also the septum 42 of the connector 40. Penetration of the needle 44 is carried out until the needle also pierces through the locking washer 29 and communicates with the interior of the tubular member 41. The needle 44 is then rotated, as above, in order to bring about a releasable locking engagement with the locking washer 29.

Typically, prior to insertion of the needle assembly, the exposed surfaces of the septum 46 on the needle assembly and the septum 42 of the connector are swiped with a suitable bactericide.

Figure 8:
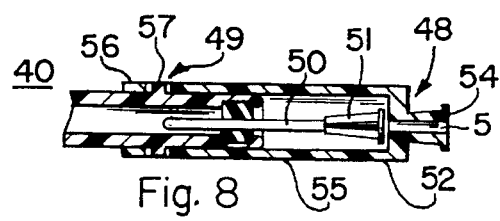
FIG. 8 illustrates a cross-sectional view of a modified connection in accordance with the invention employing an external locking means.

Referring to FIG. 8, a connection may be made with a connector 40 and a needle assembly 48 employing an external locking means 49 or mechanism. For example, as shown, the connector 40 is of a type similar to that described above with respect to FIG. 5. In this regard, the connector 40 has a tubular member 41 in which a septum 42 is recessed. In addition, the needle assembly 48 is of a type similar to FIG. 2 wherein a hollow needle 50 is mounted on a hub 51. The hub 51, in turn, is mounted on or within a housing 52 which has a bore 53 extending therethrough to a female luer connector 54.

As shown, the external locking means 49 includes a sleeve 55 which extends from the needle assembly in a manner such that the needle 50 is recessed within the sleeve 55. In this way, the sleeve 55 forms a protective shield to prevent exposure of the tip of the needle 50. In addition, the sleeve 55 is provided with one or more bayonet-type slots 56, for example, a slot having an L-shape with the long leg of the slot being disposed longitudinally of the sleeve 55 and exposed at the terminal end of the sleeve. A short transverse portion of the slot 56 is located in spaced relation to the terminal end of the sleeve 55. In addition, the locking means 49 employs one or more protuberances 57 on the outside of the tubular member 41 of the connector 40 to cooperate with the slot(s) 56.

In use, the needle assembly 48 is first placed over the end of the tubular member 41 and pushed forwardly relative thereto so that the needle 50 penetrates through the septum 42. After a certain degree of movement, the slots 56 in the sleeve 55 are aligned with the protuberances 57 of the tubular member 41 so that he protuberances 57 pass into the slots upon continued forward movement of the needle assembly 48. When the protuberances 57 reach the transverse portions of the slots 56, the needle assembly 48 is rotated thereby locking the needle assembly 48 to the connector 40.

It is to be noted that the external locking mechanism 49 is of conventional type. However, in this embodiment, the septum 42 is slit and the hollow needle 50 is provided with smooth septum-penetrating surfaces, such as those illustrated in any one of FIGS. 9 to 12.

Figure 13:
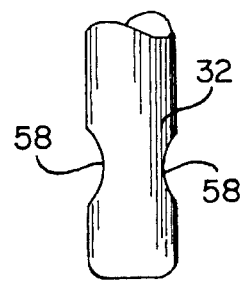
FIG. 13 illustrates an enlarged view of a dimpled end of a needle in accordance with the invention.
Figure 14:
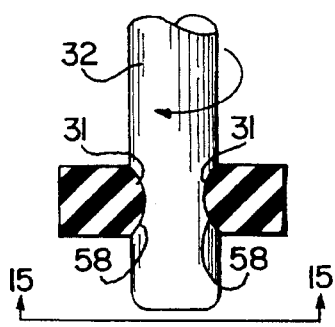
FIG. 14 illustrates an enlarged part-cross sectional view of the dimpled needle of FIG. 13 mounted within a modified locking washer in accordance with the invention.
Figure 15:
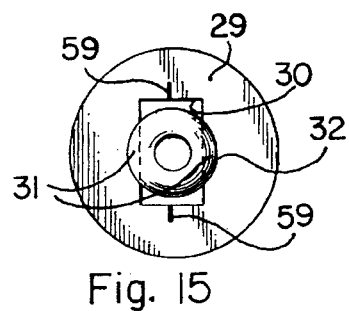
FIG. 15 illustrates a view of the arrangement of FIG. 13.
Figure 18:
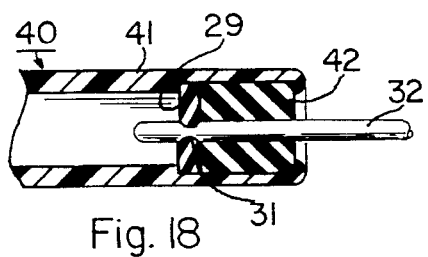
FIG. 18 illustrates an enlarged view of a needle locked in place in a connector.

Referring to FIG. 13, wherein like reference characters indicate like parts as above, the needle 32 is provided with one or more dimples, for example, two oppositely disposed dimples 58. The dimples 58 are positioned so that they can be disposed within the plane of the locking washer 29 when the needle 32 is in place. As indicated in FIGS. 13 and 15, the locking washer 29 has a bore 30 of rectangular shape in order to receive the needle 32. In this regard, the length of the bore 30 is greater than the diameter of the needle 32 while the width of the bore 30 is less than the diameter of the needle 32. When the needle 32 is in a locked position as indicated in FIGS. 14, 15 and 18, the long side walls of the washer 29 act as the protuberances 31 which pass into the dimples 58 of the needle 32.

Figure 16:
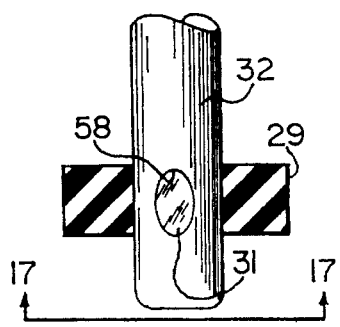
FIG. 16 illustrates a view similar to FIG. 14 with the dimpled needle in an unlocked position in the locking washer.
Figure 17:
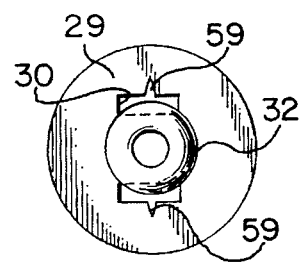
FIG. 17 illustrates a view taken on line 17—17 of FIG. 16.

As illustrated in FIG. 15, the locking washer 29 is provided with a pair of slits 59 in the walls defining the short side of the rectangular bore 30. These slits 59 allow the lock washer 29 to stretch open when the needle 32 is being passed through the bore 30. For example, as shown in FIG. 17, when a needle 32 passes into the lock washer 29, since the needle 32 is of a greater diameter than the width of the bore 30, the lock washer 29 stretches or deforms so as to enlarge the short side walls of the bore 30. When the dimples 58 of the needle 32 move into the plane of the washer 29 as indicated in FIGS. 16 and 17, the washer 29 remains in the deformed state while squeezing down on the needle 32. However, when the needle 32 is then rotated so that the walls defining the long side of the bore 30 move into the dimples 58, the lock washer 29 relaxes back into the unstressed state indicated in FIG. 15. At this time, the slits 59 close up while the long walls of the bore 30 lock into the dimples 59 of the needle 32.

Various modifications may be made within the above constructions. For example, the septum may be employed in a manner such that the septum is coaxially compressed or circumferentially compressed by a suitable means (not shown).

Various tests were conducted to determine the amount of debris caused by the smooth tipped needles of the invention. As a result of the tests, it has been found that smooth tipped hollow needles in accordance with the invention used with known slit septums, for example, an Abbott Slit Sleeve Stopper created no debris of a size greater than 0.005 inches after 25 piercings of the stopper. In this regard, the hollow needles were provided with a silicone coating in a conventional manner. By way of comparison, an Abbott Locking Blunt Cannula with the same stopper produced one particle of a size greater than 0.005 inches while producing eight particles of less than 0.005 inches while the blunt needle of the invention produced no particles greater than 0.005 inches and only one particle of less than 0.005 inches while another blunt needle of the invention produced two only particles of less than 0.005 inches and no particles of greater than 0.005 inches.

A test report detailing the test results is being filed herewith in a Preliminary Amendment.

The invention thus provides a needle and septum arrangement wherein the risk of debris being caused after repeated penetrations of the needle through the septum is reduced, if not eliminated.

Further, the invention provides a relatively simple locking mechanism for locking a needle relative to a penetrated septum.

The invention further allows a connector employing a slit septum to have an extended use.

What is claimed is:

1. The combination of a septum of elastomeric material having a slit therein and being of a thickness of from 0.074 inches to 0.160 inches; and a hollow needle for penetrating said septum through said slit, said needle having an outside diameter in a range of from 0.032 inches to 0.058 inches and a closed distal end with a smooth surface for penetrating into said septum without removing debris from said septum, said needle having at least one opening in a sidewall thereof for the passage of fluid into or from within said needle.

2. The combination as set forth in claim 1 wherein said distal end of said needle is of hemispherical shape.

3. The combination as set forth in claim 1 wherein said distal end of said needle has a flattened transverse surface and a rounded periphery extending from said transverse surface to a sidewall of said needle.

4. The combination as set forth in claim 1 wherein said septum is coaxially compressed.

5. The combination as set forth in claim 1 wherein said septum is circumferentially compressed.

6. The combination as set forth in claim 1 wherein said septum is of cylindrical shape with an outside diameter in a range of from ¼ to ½ inches.

7. The combination of a tubular member for conducting fluid therethrough;

an elastomeric septum secured to one end of said tubular member to seal said end to the passage of fluid;

a hollow needle for penetrating said septum to communicate with the interior of said tubular member; and means in said tubular member for releasably locking said needle in said tubular member after penetration through said septum to prevent accidental withdrawal of said needle from said tubular member.

8. The combination as set forth in claim 7 wherein said needle has at least one dimple in a side wall thereof and said means includes a washer having at least one protuberance for engaging in said dimple of said needle.

9. The combination as set forth in claim 8 wherein said washer is spaced from said septum.

10. The combination as set forth in claim 7 wherein said septum has a slit and said needle has a closed distal end with a smooth surface for penetrating into said septum without removing debris from said septum, said needle having at least one opening in a sidewall thereof for the passage of fluid into or from within said needle.

11. The combination as set forth in claim 10 wherein said distal end of said needle is of hemispherical shape.

12. The combination as set forth in claim 10 wherein said distal end of said needle has a flattened transverse surface and a rounded periphery extending from said transverse surface to a sidewall of said needle.

13. The combination as set forth in claim 7 wherein said septum has a slit and said needle has an open distal end for passage of fluid therethrough, said distal end having a peripheral wall terminating in a smooth rounded surface at said end for penetrating into said septum without removing debris from said septum.

14. The combination as set forth in claim 13 wherein said peripheral wall is of uniform thickness.

15. The combination as set forth in claim 13 wherein said peripheral wall is folded inwardly to define said rounded surface.

16. The combination of a tubular member for conducting fluid therethrough;

an elastomeric septum secured to one end of said tubular member to seal said end to the passage of fluid, said septum having a slit therein and being of a predetermined thickness;

a hollow needle for penetrating said slit and said septum, said needle having an outside diameter of a size less than said thickness of said septum and having one of a closed distal end with a smooth surface and an open distal end having a peripheral wall terminating in a smooth rounded surface for penetrating into said slit without removing debris from said septum; and means in for releasably locking said needle in said tubular member after penetration through said septum.

17. The combination as set forth in claim 16 wherein said means is disposed inside said tubular member.

18. The combination as set forth in claim 17 wherein said needle has at least one dimple in a side wall thereof and said means includes a washer having at least one protuberance for engaging in said dimple of said needle.

* * * * *

UNITED STATES PATENT AND TRADEMARK OFFICE
CERTIFICATE OF CORRECTION

PATENT NO. : 5,575,769
DATED : November 19, 1996
INVENTOR(S) : Vincent L. Vaillancourt It is certified that error appears in the above-indentified patent and that said Letters Patent is hereby corrected as shown below:

Column 1, line 39, change "silver" to -- sliver--.

Column 10, line 10, cancel "in"--. (1st occurrence).

Signed and Sealed this

Eleventh Day of March, 1997

Attest:

BRUCE LEHMAN

*Attesting Officer*  *Commissioner of Patents and Trademarks*